United States Patent
Hogendoorn et al.

(10) Patent No.: US 9,835,484 B2
(45) Date of Patent: Dec. 5, 2017

(54) NUCLEAR MAGNETIC FLOWMETER AND METHOD FOR OPERATING A NUCLEAR MAGNETIC FLOWMETER

(71) Applicant: Krohne AG, Basel (CH)

(72) Inventors: Cornelis Johannes Hogendoorn, Sijk (NL); Marco Leendert Zoeteweij, Hendrik-Ido-Ambach (NL); Olaf Jean Paul Bousché, Dordrecht (NL); Rutger Reinout Tromp, Dordrecht (NL); Lucas Matias Ceferino Cerioni, Dordrecht (NL)

(73) Assignee: Krohne AG, Basel (CH)

( * ) Notice: Subject to any disclaimer, the term of this patent is extended or adjusted under 35 U.S.C. 154(b) by 430 days.

(21) Appl. No.: 14/719,806

(22) Filed: May 22, 2015

(65) Prior Publication Data

US 2015/0338256 A1 Nov. 26, 2015

(30) Foreign Application Priority Data

May 23, 2014 (DE) .................. 10 2014 007 509
Jul. 14, 2014 (DE) .................. 10 2014 010 324

(51) Int. Cl.
*G01V 3/00* (2006.01)
*G01F 1/58* (2006.01)
(Continued)

(52) U.S. Cl.
CPC ............... *G01F 1/58* (2013.01); *G01F 1/716* (2013.01); *G01R 33/307* (2013.01); *G01R 33/56308* (2013.01); *G01N 24/081* (2013.01)

(58) Field of Classification Search
CPC ........... G01F 1/716; G01F 1/58; G01N 24/08; G01N 24/081; G01R 33/56308; G01R 33/307; G01R 33/5608
See application file for complete search history.

(56) References Cited

U.S. PATENT DOCUMENTS 4,862,080 A 8/1989 Van As
6,952,096 B2 10/2005 Freedman
(Continued)

OTHER PUBLICATIONS

Jankees Hogendoorn et al, Magnetic Resonance Technology—A New Concept for Multiphase Flow Measurement, 31st International North Sea Flow Measurement Workshop, Oct. 2013, Tønsberg, Norway.*

*Primary Examiner* — Daniel Miller
(74) *Attorney, Agent, or Firm* — David S. Safran

(57) ABSTRACT

A nuclear magnetic flowmeter (1) for determining the flow of a medium flowing through a measuring tube (2), having a magnetic field generator (3) having permanent magnets for generating a magnetic field interfusing the medium over a magnetic field section $L_M$, having a pre-magnetization section $L_{VM}$ located within the magnetic field section $L_M$ and having a measuring device also located in the magnetic field section $L_M$ including a coil-shaped antenna (4) with the length $L_1$ serving as a measuring antenna. At least one coil-shaped antenna (5) is provided in the pre-magnetization section $L_{VM}$ for generating a pulse or pulse sequence spoiling the magnetization of the medium in the direction of the magnetic field.

18 Claims, 2 Drawing Sheets

(51) Int. Cl.
 *G01R 33/30* (2006.01)
 *G01F 1/716* (2006.01)
 *G01R 33/563* (2006.01)
 G01N 24/08 (2006.01)

(56) References Cited

U.S. PATENT DOCUMENTS

| | | |
|---|---|---|
| 7,872,424 B2 | 1/2011 | Sun et al. |
| 8,633,689 B2 | 1/2014 | Li et al. |
| 2010/0264916 A1* | 10/2010 | Pusiol .................... G01R 33/44 324/306 |
| 2012/0174684 A1 | 7/2012 | Pusiol |

* cited by examiner

NUCLEAR MAGNETIC FLOWMETER AND METHOD FOR OPERATING A NUCLEAR MAGNETIC FLOWMETER

BACKGROUND OF THE INVENTION

Field of the Invention

The invention relates to a nuclear magnetic flowmeter for determining the flow of a medium flowing through a measuring tube, having a magnetic field generator consisting of permanent magnets for generating a magnetic field interfusing the medium over a magnetic field section, having a pre-magnetization section located within the magnetic field section and having a measuring device also located in the magnetic field section $L_M$ including a coil-shaped antenna with the length serving as a measuring antenna. Furthermore, the invention relates to a method for operating a nuclear magnetic flowmeter.

Description of Related Art

The atomic nuclei of the elements having nuclear spin also have a magnetic moment caused by nuclear spin. Nuclear spin can be regarded as angular momentum describable by a vector, and accordingly, the magnetic moment can also be described by a vector, which is aligned parallel to the vector of the angular momentum. The vector of the magnetic moment of an atomic nucleus, in the presence of a macroscopic magnetic field, aligns itself parallel to the vector of the macroscopic magnetic field at the location of the atomic nucleus. The vector of the magnetic moment of the atomic nucleus precesses around the vector of the macroscopic magnetic field at the location of the atomic nucleus. The frequency of precession is the Larmor frequency $\omega_L$ and is proportional to the magnitude of the magnetic field strength B. The Larmor frequency is calculated according to $\omega_L = \gamma \cdot B$, with $\gamma$ being the gyromagnetic ratio, which is at a maximum for hydrogen nuclei. The gyromagnetic ratio indicates the proportionality factor between the angular momentum or the spin of a particle and the associated magnetic moment.

Measuring and analyzing methods that utilize the precession of the atomic nuclei with a magnetic moment in the presence of a macroscopic magnetic field are referred to as nuclear magnetic resonance measuring or analyzing methods. This is called nuclear magnetic resonance (NMR).

A requirement for an analysis of a multi-phase medium using nuclear magnetic resonance is that the phases to be analyzed of the medium are able to be excited to distinguishable nuclear magnetic resonances. The analysis can include the flow velocities of the individual phases of the medium and the relative proportions of individual phases in the multiphase medium. Nuclear magnetic flowmeters can, for example, be used for analysis of multiphase mediums extracted from oil sources. The medium, then, consists essentially of the phases crude oil, natural gas and salt water, wherein all phases include hydrogen atom nuclei.

The analysis of the medium extracted from oil sources can be performed using so-called test separators. These divert a small amount of the extracted medium, separate the individual phases of the medium from one another and determine the proportions of the individual phases in the medium. However, test separators are not able to reliably measure crude oil proportions of less than 5%. Since the crude oil proportions are continuously sinking in all sources and the crude oil proportion of many sources is already less than 5%, it is not possible at this time to economically exploit these sources using test separators. In order to further exploit sources having even a very small crude oil proportion, accordingly exact flowmeters are necessary.

Normally, electric signals induced in a measuring antenna from the precessing atomic nuclei after excitation are used as the dependent variable for evaluation. A requirement for the measurement of a multi-phase medium is, as described above, that the individual phases of the medium can be excited to distinguishable nuclear magnetic resonances. The magnitude of the electric signal induced in the measuring antenna from the precessing atomic nuclei of a phase of the medium is dependent on the number of precessing atomic nuclei per volume element in this phase, hence dependent on the density of the phase, but also on the impact time of the atomic nucleus in the influencing magnetic field. Consequently, the magnitude of the induced electric signal is different for each phase of the medium.

Measuring methods for determining the individual phases of the medium provide that the medium is exposed to the magnetic field generated in the pre-magnetization section for a certain time, and then, the magnetization of the medium in the direction of the magnetic field is determined after different lengths of exposure of the magnetic field generated in the pre-magnetization section on the medium. Determining the magnetization of the medium after a certain impact time occurs in the measuring device by exciting the magnetized medium with excitation signals, measuring the measuring signals caused by the excitation signals in the medium and evaluating the measuring signals.

Nuclear magnetic flowmeters known from the prior art of the type described in the introduction vary the effective impact time of the magnetic field on the medium by changing the magnetic field, wherein the changing of the magnetic field is caused by a mechanism.

A nuclear magnetic flowmeter of the type described in the introduction is known from U.S. Pat. No. 7,872,424. The magnetic field generator includes several consecutive magnet arrangements arranged around the measuring tube along the longitudinal axis of the measuring tube. Each of the magnet arrangements is turnable around the longitudinal axis of the measuring tube and interfuses the medium flowing through the measuring tube with a magnetic field demonstrating a certain direction. The effective pre-magnetization section is then varied in that each of the magnetic fields of the individual magnet arrangements are aligned parallel or antiparallel to one another. In a parallel alignment of two magnetic fields each generated by one magnet arrangement, the magnetization in the medium builds up over the time, it takes, until the medium has flowed through both magnet arrangements. In an antiparallel alignment of two magnetic fields the magnetization in the medium builds up in the first magnet arrangement and is destroyed in the second magnet arrangement due to the opposing field direction in an antiparallel alignment of two adjacent magnetic fields. In this case, the effective pre-magnetization section is zero.

Turning each magnet assembly requires a mechanism. This mechanism requires, on the one hand, space, and on the other hand, is associated with costs. Additionally, mechanically moving parts are subject to normal wear and tear and need to be maintained on a regular basis. This means efforts in both time and cost.

A device for varying the pre-magnetization section is also known from the prior art, in which several magnet arrangements are arranged around the measuring tube. Each of these magnet arrangements consists of an inner ring of a permanent-magnetic material and an outer ring also of a permanent-magnetic material. Each of these rings generates a magnetic field. Both rings can be shifted relative to one another. If the rings are located in a position relative to one another so that both magnetic fields are aligned parallel to one another, then there is a strong magnetic field within the magnet arrangement. If the two rings are aligned relative to one another so that the two magnetic fields are antiparallel to one another, then the field within the magnet arrangement is zero. By arranging several such magnet arrangements consecutively, the effective pre-magnetization section can be arbitrarily varied.

Here, the pre-magnetization section is also set by a mechanism which turns each of the rings of a magnet arrangement in opposite directions. This requires a generous amount of time and the moving components require maintenance on a regular basis, which is associated with a higher investment in time and costs as well as wear.

SUMMARY OF THE INVENTION

A primary object of the present invention is to provide a nuclear magnetic flowmeter, in which the disadvantages of the prior art are reduced or eliminated, as well as to provide a method for operating nuclear magnetic flowmeters.

The above derived and described object is initially and essentially achieved in that at least one coil-shaped antenna is provided in the pre-magnetization section $L_{VM}$ for generating a pulse spoiling the magnetization of the medium in the direction of the magnetic field or a pulse sequence spoiling the magnetization of the medium in the direction of the magnetic field, summarized in the following as spoiling pulse. The antenna can be arranged around the measuring tube, incidentally at an arbitrary location in the pre-magnetization section. The pulse can be generated in the direction of flow of the medium. In the following, the direction of flow of the medium is to be called x-direction, while the magnetic field generated by the magnetic field generator is generated in the z-direction, perpendicular to the direction of flow.

As opposed to the prior art, the invention has the great advantage that the length of the effective pre-magnetization section can be easily varied without requiring maintenance. If the antenna does not generate a spoiling pulse, the pre-magnetization section corresponds to the entire magnetization section up to the measuring device. If, however, the antenna generates a spoiling pulse, the magnetization in the area of the antenna is destroyed and is subsequently formed again over the remaining section between antenna and measuring device, thus shortening the effective pre-magnetization section.

The build-up of magnetization after the spoiling pulse follows the relationship:

$$M = M_0\left(1 - \exp\left(-\frac{L_{VM}}{vT_1}\right)\right)$$

Here, $L_{VM}$ is the effective pre-magnetization section, i.e., the section between the antenna emitting the spoiling pulse and the antenna in the measuring device, v is the flow velocity of the medium and $T_1$ is the spin-lattice relaxation time of the medium or the individual phases of the medium.

The flow velocity of the individual phases of a multi-phase medium does not have to be identical. In reality, the individual phases of a medium often have differing flow velocities; the flow profile thus has a maximum flow velocity $v_{max}$ and a minimum flow velocity $v_{min}$. Different flow velocities can lead to a so-called "phase slip",—a faster-flowing phase "passing" a lower-flowing phase. This effect has negative influences on flow measurement, since the impact time of the individual phase and thus the build-up of magnetization in the direction of the magnetic field is directly associated with the flow velocity of the phase in a pre-magnetization section generated by permanent magnets. A fast-flowing phase, thus, has a shorter impact time than a slow-flowing phase in the same pre-magnetization section.

Preferably, it is provided that the antenna for generating spoiling pulses is arranged at a distance d from the antenna of the measuring device and that the length $L_2$ of the antenna generating the spoiling pulse is chosen in such a manner that the following formula is fulfilled.

$$L_2 \geq 2d\left(\frac{v_{max} - v_{min}}{v_{max} + v_{min}}\right) + L_1$$

Here, $v_{max}$ is the maximum flow velocity in the flow profile, $v_{min}$ is the minimum flow velocity and $L_1$ is the length of the antenna of the measuring device. Thus, it is guaranteed that the entire medium located in the area of the measuring antenna at the time of measurement has experienced the spoiling pulse and the magnetization of each phase is formed independently of the respective flow velocity over the same amount of time, i.e., each phase experiences the same impact time of the magnetic field.

For the magnetization:

$$M = M_0\left(1 - \exp\left(-\frac{\Delta t}{T_1}\right)\right)$$

wherein $\Delta t$ is the time between the spoiling pulse and the beginning of the measuring sequence in the measuring device for determining the flow of the medium and $T_1$ is the spin-lattice relaxation time of the medium or the individual phase of the medium.

By suitably choosing the length of the antenna generating the spoiling pulse, inaccuracies in measurement can be reduced and measurements become more reliable.

In a particularly preferred design of the flowmeter according to the invention, it is provided that at least one additional coil-shaped antenna is arranged in the pre-magnetization section $L_{VM}$ for generating a pulse spoiling the magnetization of the medium in the direction of the magnetic field or a pulse sequence spoiling the magnetization of the medium in the direction of the magnetic field. At least one further effective pre-magnetization is generated thereby. The antennae can be arranged directly next to one another. However, it is possible to have one or several antennae spaced from one another. An arrangement is also possible formed of at least three antennae, in which at least two antennae are adjacent to one another and at least one further antenna is arranged spaced from the antennae adjacent to one another. Every single antenna can thereby fulfill the above-described requirements for its length $L_2$.

It is also possible to arrange several antennae (n antennae) directly adjacent to one another around the measuring tube, wherein every single antenna has a length shorter than that described above. However, it is then provided that the sum of a number k≤n of directly adjacent antennae has a length that fulfills the requirements for $L_2$. If the k antennae simultaneously generate a spoiling pulse, this is identical to a single antenna having the length of the sum of the lengths of the k antennae. Due to the arrangement of several antennae, which can have the same length or different lengths, it is possible to easily implement several effective pre-magnetization sections.

An object of the invention is also to provide a method for operating a nuclear magnetic flowmeter for determining the flow of a medium flowing through a measuring tube, namely one having a magnetic field generator consisting of permanent magnets for generating a magnetic field interfusing the medium over a magnetic field section $L_M$, having a pre-magnetization section $L_{VM}$ located within the magnetic field section $L_M$ and having a measuring device also located in the magnetic field section $L_M$ including a coil-shaped antenna with the length $L_1$ serving as a measuring antenna.

The method according to the invention is initially and essentially wherein a flowmeter is used for determining the flow, in which at least one coil-shaped antenna is provided in the pre-magnetization section $L_{VM}$ for generating pulse spoiling the magnetization of the medium in the direction of the magnetic field or a pulse sequence spoiling the magnetization of the medium in the direction of the magnetic field, that a pulse spoiling the magnetization of the medium in the direction of the magnetic field or a pulse sequence spoiling the magnetization of the medium in the direction of the magnetic field is generated with the coil-shaped antenna in the pre-magnetization section, that a waiting time $\Delta t$ is anticipated before the proper measurement and that, subsequently, a nuclear magnetic measurement is performed on the medium in the measuring device by exciting the magnetized medium by excitation signals and measuring the measuring signals caused by the excitation signals in the medium.

In a preferred implementation of the method according to the invention, in which the used flowmeter has only one single, coil-shaped antenna for generating a pulse spoiling the magnetization of the medium in the direction of the magnetic field or a pulse sequence spoiling the magnetization of the medium in the direction of the magnetic field and in which the antenna generating the spoiling pulse fulfills the requirements descried above for its length $L_2$, it is provided that the antenna located in the pre-magnetization section generates a pulse or a pulse sequence, through which the magnetization of the medium in the direction of the magnetic field, which was formed in the medium flowing through the pre-magnetization section interfused by the magnetic field, is destroyed. The magnetization in the area of length $L_3$ of the medium is destroyed, which, at the time of the pulse, is located in the part of the measuring tube that is surrounded by the antenna generating the spoiling pulse. The length of the antenna generating the spoiling pulse is $L_2$. Then, $L_3=L_2$ holds true.

In the method according to the invention, the spoiling pulse can be a P90 pulse, a P180 pulse or a saturation pulse sequence. The method according to the invention is, however, not limited to the above-mentioned types of spoiling pulses. Any pulse or pulse sequence is possible that destroys the magnetization of the medium in the direction of the magnetic field.

The method according to the invention is, as described above, not limited to the use of certain spoiling pulses. The method according to the invention is also not limited to a certain measuring sequence in the measuring device for the nuclear magnetic measurement. Here, every conceivable sequence in the scope of flow measurement is possible.

In another preferred implementation of the method according to the invention, which is particularly suitable for flow measurement of a medium with plug flow, it is provided that the wait time $\Delta t$ is determined with $\Delta t=d/v$, wherein d is the distance between the antenna generating the spoiling pulse and the antenna receiving the measuring signal and v is the flow velocity of the medium.

When the antenna generating the spoiling pulse fulfills the laws for its length, which can be provided by the invention, i.e. has a length greater than or equal to the length of the measuring antenna, precisely the part of the medium, whose magnetization was previously destroyed and re-formed, is located in the area of the measuring antenna after the wait time $\Delta t=d/v$.

In another particular implementation of the method according to the invention, which is particularly suitable for flow measurement of a medium having flow profile with a maximum flow velocity $v_{max}$ and a minimum flow velocity $v_{min}$, it is provided that the wait time $\Delta t$ is determined by $$\frac{\left(d+\frac{L_2}{2}-\frac{L_1}{2}\right)}{v_{max}} \geq \Delta t \geq \frac{\left(d-\frac{L_2}{2}+\frac{L_1}{2}\right)}{v_{min}}$$

wherein $L_2$ is the length of the antenna generating the spoiling pulse, $L_1$ is the length of the antenna in the measuring device, $v_{max}$ is the maximum flow velocity and $v_{min}$ is the minimum flow velocity. This guarantees that the entire measured area contains medium whose magnetization has been previously destroyed.

It has been shown that the impact time of the magnetic field on the medium in the area of the pre-magnetization section is independent of the flow velocity of the medium or the individual phases of the medium and independent of the flow profile for each phase when the previously-described law for wait time $\Delta t$ is observed, so that a uniform magnetization of each individual phase is guaranteed.

In the method according to the invention, a flowmeter can also be used in which more than one antenna is provided in the pre-magnetization section $L_{VM}$ generating a pulse spoiling the magnetization of the medium in the direction of the magnetic field or generating a pulse sequence spoiling the magnetization of the medium in the direction of the magnetic field and in which the antennae can be arranged directly next to one another or spaced from one another and each of the antennae has a length $L_2$, which fulfills the relationships described further above. Then, the method according to the invention can be further wherein in the first step of the method, a first antenna generates a spoiling pulse, in a second step, a wait time $\Delta t$ is anticipated, in a third step, the flow of the medium is measured in the measuring unit, in a fourth step, a second antenna generates a spoiling pulse, in a fifth step, again, a wait time $\Delta t$ is anticipated and in a sixth step, the flow of the medium is measured in the measuring unit. If more than two antenna generating spoiling pulses are provided in the used flowmeter, the first three method steps are carried out for each further antenna.

If a flowmeter is used for the method according to the invention, in which more than one antenna is provided for generating a pulse spoiling the magnetization in the direction of the magnetic field of the medium or a pulse sequence spoiling the magnetization in the direction of the magnetic field of the medium, a further teaching provides that several antennae generating spoiling pulses simultaneously generate a spoiling pulse. It is preferable, thereby, to measure the medium in the measuring device after each wait time. Thus, the time between the individual measurements is shortened to the difference between the individual wait times.

A concrete use of the method according to the invention is, for example, found in determining the spin-lattice relaxation time $T_1$:

Normally, a $T_1$ measurement is carried out with an inverse recovery experiment. After the whole magnetization, equilibrium magnetization, has been built up in the medium, the magnetization is inverted by a P180 pulse, a certain amount of time is passed, in which the magnetization can rebuild and the amount of the reproduced magnetization is measured for different recovery times. The disadvantage thereby is that the wait time until the magnetization reaches the equilibrium level again is long, before a new experiment can be carried out with another recovery time.

Now it is provided according to the invention that the magnetization in the medium is destroyed by a spoiling pulse, a certain, but pre-determined, amount of time is anticipated, wherein this wait time is not to be confused with the recovery time, in which a part of the magnetization is reproduced and then the inverse recovery experiment is carried out as described above. The time between the spoiling pulse and the beginning of the inverse recovery experiment is, according to the invention, less than the time that it takes for the equilibrium magnetization to be rebuilt. Thus, the equilibrium magnetization is replaced by a pre-determined "partial magnetization", through which the experiments with different recovery times can be carried out with less wait time.

A particularly preferred implementation of the method according to the invention is wherein n further nuclear magnetic measurements are carried out with a respective time lag $\Delta\tau$ to one another after the first nuclear magnetic measurement.

The above-described design is particularly suitable for determining the spin-lattice relaxation time $T_1$ of the medium in a very simple manner. The magnetization of the medium formed in the pre-magnetization section is destroyed by a pulse spoiling the magnetization in the direction of the applied magnetic field or a pulse sequence spoiling the magnetization in the direction of the applied field over a spatial section $L_3$.

The magnetization is formed according to the above-described law parallel to the outer applied magnetic field slowly over time. After a first time $\Delta t$ after the spoiling pulse, the magnetization has reached a certain value. After each additional time $\Delta\tau$, the magnetization is further formed and has an increasing value until the equilibrium magnetization $M_0$ is achieved. After each time $\Delta\tau$, a nuclear magnetic measurement is carried out and the medium that "just" flowed into the area of the measuring coil is thus measured, in that, in particular, the magnetization is further formed with the passing of time. In particular, it can be provided to carry out a FID measurement (free induction decay) and thus to measure the amplitude of the magnetization of the medium that just flowed into the area of the measuring coil. Since the forming of magnetization is determined by the spin-lattice relaxation time $T_1$, this can be easily determined from the recorded measuring values. Thus, this preferred design has the particular advantage of being able to determine the spin-lattice relaxation time $T_1$.

In detail, there are various possibilities for designing and further developing the nuclear magnetic flowmeter and the method according to the invention as will be apparent from the following description of preferred embodiments in conjunction with the accompanying drawings.

DETAILED DESCRIPTION OF THE INVENTION

Figure 1:
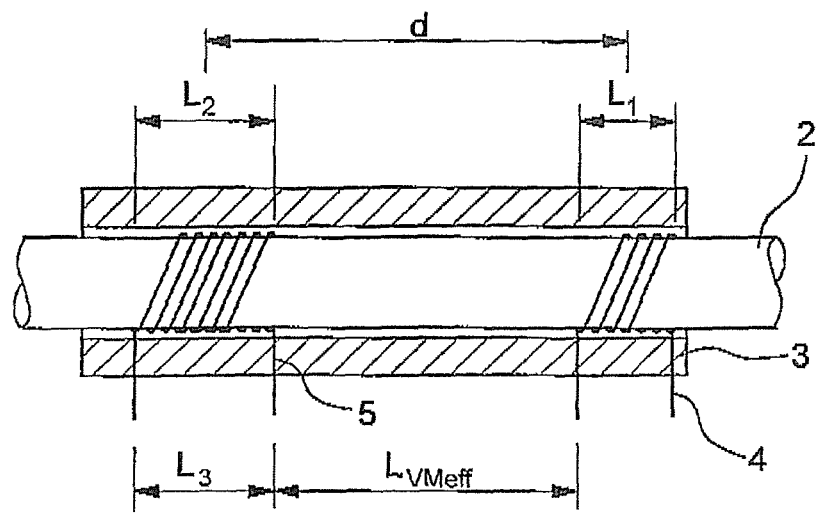
FIG. 1 shows a first embodiment of a nuclear magnetic flowmeter according to the invention.
Figure 3:
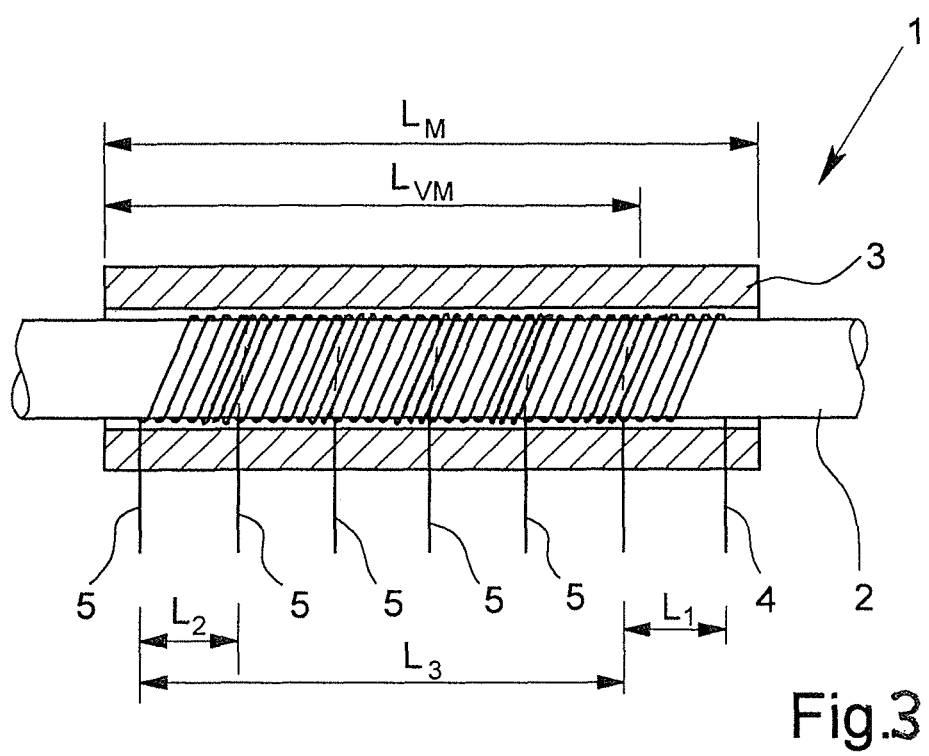
FIG. 3 shows a third embodiment of a nuclear magnetic flowmeter according to the invention.

The essential elements of a first embodiment of a nuclear magnetic flowmeter 1 according to the invention are shown in FIG. 1. The nuclear magnetic flowmeter 1 has a measuring tube 2 with medium flowing through it, whose flow is to be determined. The medium can include one or several phases. For determining the flow, the nuclear magnetic flowmeter 1 has a magnetic field generator 3, which is arranged around the measuring tube 2. The magnetic field generator, which can comprise one or more permanent magnets, generates a magnetic field that interfuses the measuring tube 2 over a magnetic field section $L_M$. A coil-shaped antenna 4 is provided at the rearward end of the magnetic field generator 3 in terms of flow direction of the medium, which is used for generating excitation pulses exciting the medium as well as for detecting measuring signals caused by the excitation signals in the medium. The coil-shaped antenna 4 has a length $L_1$. The section interfused with the magnetic field in front of the coil-shaped antenna 4 is used for pre-magnetization of the medium flowing through the measuring tube 2 and is called pre-magnetization section $L_{VM}$. A coil-shaped antenna 5, which is arranged around the measuring tube 2, is provided in the pre-magnetization section $L_{VM}$ according to the invention. The coil-shaped antenna 5 generates a pulse spoiling the magnetization of the medium in the direction of the magnetic field generated by the magnetic field generator 3 or a pulse sequence spoiling the magnetization of the medium in the direction of the generated magnetic field and has a length $L_2$. The magnetization of the medium is destroyed for a section $L_3$ of the medium. In FIG. 3, the situation is shown in which the section of the destroyed magnetization $L_3$ corresponds to the length $L_2$ of the antenna 5.

After the magnetization of the medium has been destroyed, it is formed again in the magnetic field generated by the magnetic field generator 3. This occurs in an effective pre-magnetization section $L_{VMeff}$ between the antenna 5 and the antenna 4. The antenna 5 generating the spoiling pulse is spaced from the measuring antenna 4 by a distance d.

Figure 2:
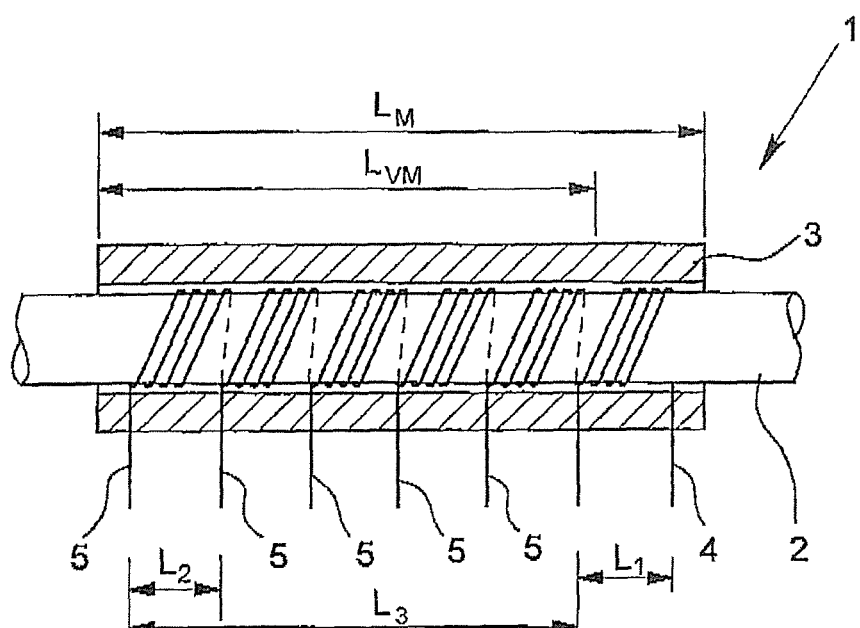
FIG. 2 shows a second embodiment of a nuclear magnetic flowmeter according to the invention.

A further embodiment of the nuclear magnetic flowmeter 1 according to the invention is shown in FIG. 2. The same elements have the same reference numbers in both embodiments.

The fundamental difference between the embodiment shown in FIG. 1 and the embodiment shown in FIG. 2 is that several coil-shaped antennae 5 are provided for generating a pulse spoiling the magnetization of the medium or pulse sequence spoiling the magnetization of the medium. The antennae 5 are arranged around the measuring tube 2. FIG. 2 shows five such antennae 5. The antennae 5 are arranged spaced from one another, around the measuring tube 2.

FIG. 3 shows a third embodiment of the nuclear magnetic flowmeter 1 in which the same elements as shown in FIG. 2 have the same reference numbers. This embodiment differs from that of FIG. 2 only in that the coil-shaped antennae are arranged directly adjacent to one another in the direction of flow of the medium instead of being spaced from each other. If all antennae simultaneously generate a spoiling pulse, section $L_3$ is the area of the pre-magnetization section, in which the magnetization of the medium has been destroyed.

What is claimed is:

1. A nuclear magnetic flowmeter for determining the flow of a medium flowing through a measuring tube, having a magnetic field generator comprised of permanent magnets for generating a magnetic field interfusing the medium over a magnetic field section $L_M$, having a pre-magnetization section $L_{VM}$ located within the magnetic field section $L_M$ and having a measuring device also located in the magnetic field section $L_M$, the measuring device having at least one coil-shaped antenna with the length $L_1$ serving as a measuring antenna, wherein at least one additional coil-shaped antenna is provided in the pre-magnetization section $L_{VM}$ for generating a pulse or pulse sequence spoiling magnetization of the medium in a direction of the magnetic field.

2. The nuclear magnetic flowmeter according to claim 1, wherein the coil-shaped antenna has a length $L_2$ that has been set in accordance with the relationship:

$$L_2 \geq 2d\left(\frac{v_{max} - v_{min}}{v_{max} + v_{min}}\right) + L_1$$

wherein d is a distance between the measuring antenna and the coil-shaped antenna, $v_{max}$ is the maximum flow velocity, $v_{min}$ is the minimum flow velocity and $L_1$ is the length of the measuring antenna.

3. The nuclear magnetic flowmeter according to claim 1, wherein the at least one additional coil-shaped antenna comprises a plurality of additional coil-shaped antennae provided in the pre-magnetization section L.sub.VM for generating a pulse or pulse sequence spoiling the magnetization of the medium in the direction of the magnetic field.

4. The nuclear magnetic flowmeter according to claim 3, wherein the coil-shaped antennae are arranged directly adjacent to one another in the direction of flow of the medium.

5. The nuclear magnetic flowmeter according to claim 3, wherein the coil-shaped antennae are arranged spaced from one another in the direction of flow of the medium.

6. The nuclear magnetic flowmeter according to claim 3, wherein the coil-shaped antennae are arranged partially directly adjacent to and partially spaced from one another.

7. The nuclear magnetic flowmeter according to claim 3, wherein the coil-shaped antennae have the same length.

8. The nuclear magnetic flowmeter according to claim 3, wherein the coil-shaped antennae have different lengths.

9. A method for operating a nuclear magnetic flowmeter for determining the flow of a medium flowing through a measuring tube, having a magnetic field generator comprised of permanent magnets for generating a magnetic field interfusing the medium over a magnetic field section $L_M$, having a pre-magnetization section $L_{VM}$ located within the magnetic field section $L_M$ and having a measuring device also located in the magnetic field section $L_M$ including at least one coil-shaped antenna with the length $L_1$ serving as a measuring antenna, comprising the steps of:

generating a spoiling pulse or spoiling pulse sequence with at least one additional coil-shaped antenna being located in the pre-magnetization section that spoils magnetization of the medium in the direction of the magnetic field in the pre-magnetization section, waiting a time $\Delta t$ before measuring the flow of the medium and subsequently, performing a nuclear magnetic measurement of the medium in the measuring device by exciting the magnetized medium with excitation signals and measuring measurement signals produced in the medium by the excitation signals.

10. The method according to claim 9, wherein the spoiling pulse or spoiling pulse sequence is one of P90 pulse, a P180 pulse and a saturation pulse sequence.

11. The method according to claim 9, wherein the medium flowing through the measuring tube has a flow profile with a maximum flow velocity $v_{max}$ and a minimum flow velocity $v_{min}$, wherein the waiting time $\Delta t$ is selected in accordance with the relationship:

$$\frac{\left(d + \frac{L_2}{2} - \frac{L_1}{2}\right)}{v_{max}} \geq \Delta t \geq \frac{\left(d - \frac{L_2}{2} + \frac{L_1}{2}\right)}{v_{min}}$$

wherein d is the distance between the measuring antenna and the coil-shaped antenna, $L_2$ is the length of the coil-shaped antenna and $L_1$ is the length of the measuring antenna.

12. The method according to claim 9, wherein said spoiling pulse or spoiling pulse sequence for spoiling the magnetization of the medium in the direction of the magnetic field is produced by a plurality of coil-shaped antennae which simultaneously generate pulses.

13. The method according to claim 9, wherein said spoiling pulse or spoiling pulse sequence for spoiling the magnetization of the medium in the direction of the magnetic field is produced by a plurality of coil-shaped antennae which generate pulses staggered in time.

14. The method according to claim 9, wherein said spoiling pulse or spoiling pulse sequence for spoiling the magnetization of the medium in the direction of the magnetic field is produced by a plurality of coil-shaped antennae which are spaced from each other.

15. The method according to claim 9, wherein said at least one additional coil-shaped antenna is a plurality of coil-shaped antennae which are directly adjacent to each other for producing said spoiling pulse or spoiling pulse sequence for spoiling the magnetization of the medium in the direction of the magnetic field.

16. The method according to claim 9, wherein said at least one additional coil-shaped antenna is a plurality of coil-shaped antennae which are partially directly adjacent and partially spaced from each other for producing said spoiling pulse or spoiling pulse sequence for spoiling the magnetization of the medium in the direction of the magnetic field.

17. The method according to claim 11, comprising the addition step of performing further nuclear magnetic measurements with a respective time lag $\Delta\tau$ relative to one another.

18. The method according to claim 17, wherein a spin-lattice-relaxation time T.sub.1 is determined from measured values of said further nuclear magnetic measurements.

* * * * *